United States Patent [19]

Dockhorn et al.

[11] 4,201,082

[45] May 6, 1980

[54] PROCESS AND EQUIPMENT FOR DETERMINING THE DENSITY OF A LOADED DRILLING FLUID FROM A DEEP WELL, IN PARTICULAR AN OIL WELL

[76] Inventors: Wolfgang Dockhorn, Frankenwaldstr. 13A, D-4460 Nordhorn, Fed. Rep. of Germany; Arnoldus Achterberg, Herodotuslaan 43, Assen, Netherlands

[21] Appl. No.: 908,667

[22] Filed: May 23, 1978

[30] Foreign Application Priority Data

May 25, 1977 [DE] Fed. Rep. of Germany ....... 2723618
May 18, 1978 [DE] Fed. Rep. of Germany ....... 2821746

[51] Int. Cl.² .............................................. E21B 47/06
[52] U.S. Cl. .......................................... 73/153; 73/438
[58] Field of Search ........................... 73/153, 438, 155

[56] References Cited

U.S. PATENT DOCUMENTS

| | | | |
|---|---|---|---|
| 3,514,996 | 6/1970 | Costau | 73/153 |
| 3,839,914 | 10/1974 | Modisette et al. | 73/438 |
| 3,911,740 | 10/1975 | Calhoun | 73/153 |

*Primary Examiner*—Jerry W. Myracle
*Attorney, Agent, or Firm*—Andrus, Sceales, Starke & Sawall

[57] ABSTRACT

Process and apparatus for determining the density of oil well drilling fluid, particularly, the gas content of the fluid. The density of the drilling fluid is determined under a known pressure. The drilling fluid is compressed and the density of the compressed fluid determined. An indication of the gas content derived from the difference between the measured densities.

18 Claims, 5 Drawing Figures

PROCESS AND EQUIPMENT FOR DETERMINING THE DENSITY OF A LOADED DRILLING FLUID FROM A DEEP WELL, IN PARTICULAR AN OIL WELL

BACKGROUND OF THE INVENTION

1. Field of the Invention

The invention relates to a process for determining the density of a loaded drilling fluid from a deep well, in particular an oil well. Additionally, the invention relates to equipment for carrying out this process.

2. Description of the Prior Art

In deep-drilling, the drilling fluid is, inter alia, used for conveying the drillings out of the well. At the same time, however, it also absorbs other materials, for example gases, water or the like, and entrains them up to the surface. The nature and amount of such materials contained in the drilling fluid make it possible to draw certain conclusions, inter alia, on the type of the geological strata which are cut through by the well, and also on possible blow-outs which endanger the well.

It is known to monitor the drilling fluid continuously by determining its specific gravity or its density in order to be able to draw conclusions on the gas content in this way. For this purpose, the pressure of the drilling fluid is determined in a section of the length of a column of drilling fluid at two points which are offset in height, and its temperature is determined between the pressure-measuring points. The specific gravity is obtained by forming a differential pressure value, and this is compensated using the measured temperature (DT-OS 2,507,026). The characteristic of the known process is the determination of the specific gravity of the drilling fluid in absolute values so that the measured pressures must be compensated using a measured temperature value. Thus, in addition to the gas content, other influences on the density of the drilling fluid also enter into the measurement. These include waters from the strata, slurries of different drillings or the like. Since, frequently, it is precisely the gas content which matters, and other influences are superimposed on the influence of the gas content on the density of the drilling fluid, more accurate information cannot be obtained by the known process.

SUMMARY OF THE PRESENT INVENTION

It is the object of the invention to determine the gas content of the drilling fluid quantitatively, and in a further embodiment to determine it also qualitatively, in such a way that, by contrast, the influences of other, that is to say non-gaseous, admixtures to the drilling fluid are suppressed.

According to the invention, this object is achieved when the density of the drilling fluid which is under a known pressure is determined and the drilling fluid is then compressed, whereupon the density of the compressed drilling fluid is determined and the gas content is derived from the differences between the measured densities.

Since the densities of the drilling fluid under different pressures are determined simultaneously or immediately following one another, it is not necessary to know the exact specific gravity of the drilling fluid to be measured. Rather, a relative value is derived, and the difference between these relative values follows from the pressure difference. Since the pressure difference now merely influences the gas contained in the drilling fluid, the remaining influences which effect a change in density are eliminated. The process according to the invention has therefore the advantage that its engineering design can be particularly simple and that it can thus be carried out at the well head itself. Furthermore, the measurements can accordingly be carried out at any desired frequency and the characteristic data can be made available immediately at the well head.

According to a preferred embodiment of the invention, the hydrostatic pressures of columns of drilling fluid are in each case determined at least at two measuring points located at a known vertical distance from one another; the pressure measurements are here carried out in a pipe carrying the drilling fluid under normal pressure and in a pipe carrying the compressed drilling fluid. This process makes it possible to carry out the measurement in a unit through which the drilling fluid or a branched-off part of the drilling fluid flows.

A further simplification results when the measuring points of one pipe are located at the same level as the measuring points of the other pipe since, in this way, hydrostatic differences can be eliminated and it is merely the compression pressure which determines the pressure differences.

BRIEF DESCRIPTION OF THE DRAWINGS

The details and further features of the invention can be seen from the description which follows of equipment for carrying out the new process, by reference to the drawings in which.

DETAILED DESCRIPTION OF THE PREFERRED EMBODIMENT

Figure 1:
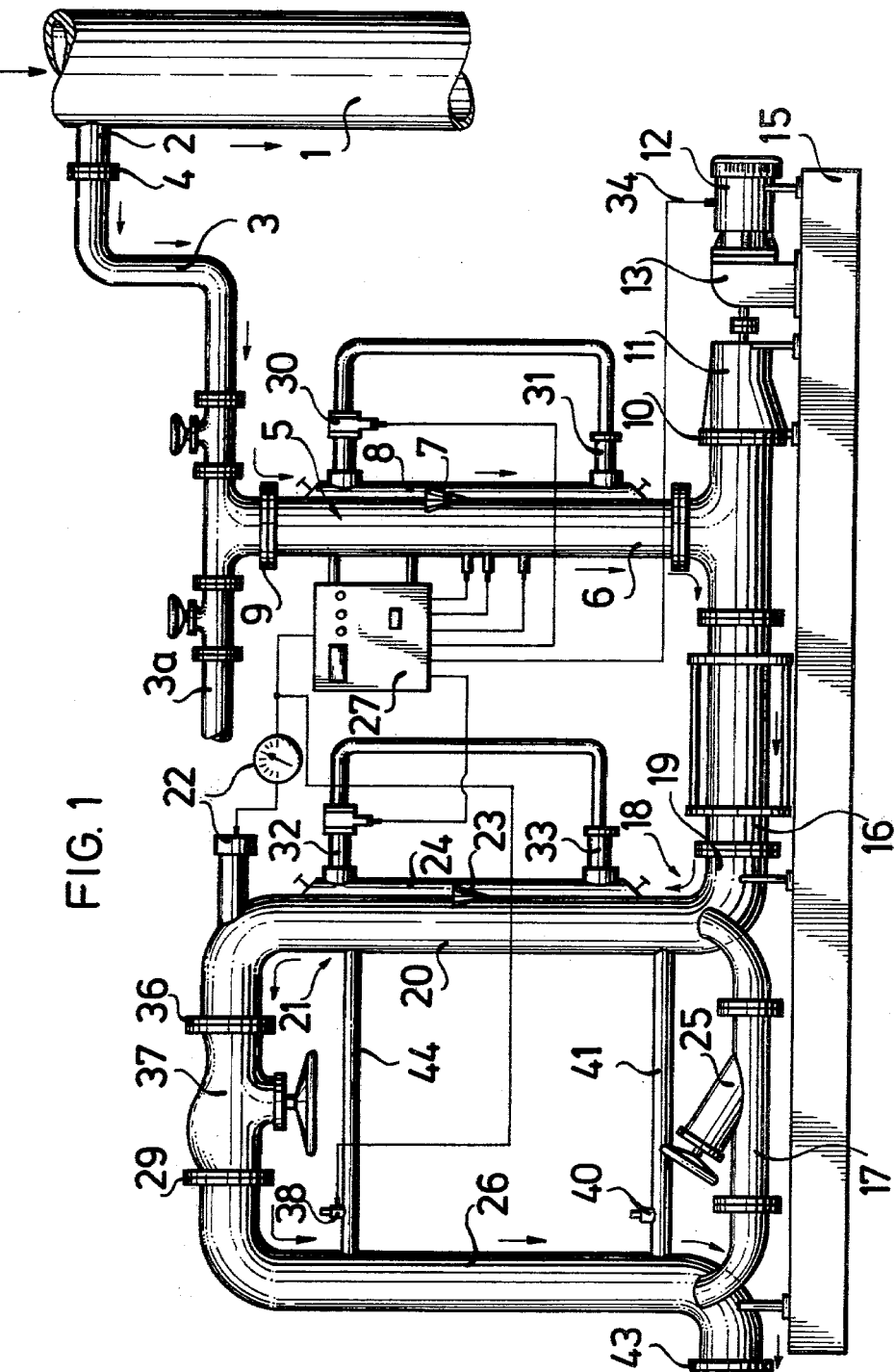
FIG. 1 shows the equipment according to the invention diagrammatically, that is to say omitting all the details which are not required for understanding the invention.

The drilling fluid coming to the surface from a deep well is present in a standpipe 1. Above a blow-out preventer which is not shown and below the drilling fluid outlet, a nozzle 2 branches off. A connecting pipe 3 is flanged at 4 to the nozzle 2. From the nozzle 3, the drilling fluid enters the actual measuring equipment through an isolation valve under a given pressure, that is to say a known and relatively low pressure; the measuring equipment can be by-passed and drained through a nozzle 3a.

The measuring path comprises above all a U-shaped pipe length generally designated as 5. This pipe length has a first pipe 6 which forms one arm of the U-shaped arrangement. The pipe 6 has a slot, the details of which are not shown more closely, which is provided at 7 and which is closed by a screen. A half-shell 8 of pipe is welded to the pipe 6 in such a way that it covers the slot 7 and the screen. As a result of this, the drilling fluid is also present in the half-shell 8 of pipe, but it does not contain the coarse constituents (cuttings) of the drilling fluid, since these are retained by the screen.

At 9, the vertical pipe 6 is joined to the connecting pipe 3 and, at 10, it is joined to a pump 11 which is driven by an electric motor 12 via a gearbox 13. The pump is a screw pump and is in itself known so that it is not necessary to describe it in detail. In place of a screw pump, it is also possible to use a piston pump, advantageously a twin-cylinder pump. The pump is mounted on a base 15. Its delivery pipe 16 and a pipe 17, flanged thereto, conjointly form the cross-over 18 of the U-shaped measuring paths. A branch 19 is used for flanging-on a further vertical pipe 20 which in turn forms the other arm 21 of the U-shaped arrangement. A measuring arrangement, namely a manometer 22, is flanged to the free end of the pipe 20.

Like the pipe 6, the pipe 20 is also provided, at 23, with a slot which in turn is closed by a screen which is not shown. Furthermore, in the same way as in the pipe 6, the pipe 20 is also fitted with a half-shell 24 of pipe, wherein the drilling fluid is present without coarse constituents.

The pipe 20 ends in a flange 36 for an isolation valve 37 which makes it possible to isolate the flow of drilling fluid downstream of the pipe 20, but which can also release the flow of drilling fluid via a pipe 26 which is flanged on at 29. Moreover, the pipe bend consisting of the parts 20, 37 and 26 is short-circuited by a lower line 17, and an isolation valve 25 can close the by-pass.

The measured values from two pressure sensors 30 and 31 which are fitted at the known level distance on the half-shell 8 of pipe and which measure the pressure of the drilling fluid, can be fed to a computer 27. The measured pressure values from pressure sensors 32 and 33 which are fitted to the half-shell 24 of pipe at a distance, which is likewise known and, according to the illustrative embodiment shown, is the same as that of the pressure sensors 30 and 31, and which measure the pressure of the drilling fluid, are also fed to the computer 27. Moreover, the computer is connected via the line 34 to the motor 12 of the pump 11. The manometer 22 is in turn connected to the computer and to a valve 38 which is inserted into the line 44 and which closes a by-pass 44 at a pre-determined pressure and which is set to a lower pressure than a relief valve 40 in a by-pass 41.

The equipment described operates as follows:

In the half-shell 8 of pipe, the drilling fluid is under a low initial pressure which results from the level difference of the nozzle 2. Through the screen closure which preferably consists of wire, the drilling fluid passes, without the so-called cuttings, into the half-shell 8 of pipe which is welded on and hence to the sensors 30 and 31. The pressures which apply are determined electronically and fed to the computer 27.

The pump 11 extracts the solids fraction and the screened drilling fluid via the connecting pipes. This fluid is pressed into the second pipe 20, while the valve 25 is closed. A compression of the drilling fluid up to, for example, 10 bars is effected here with the aid of the pump 11. At this pressure, the pressure of the drilling fluid is measured on the sensors 32 and 33. These values are passed on to the computer 27.

Due to the valve settings in the valves 37 and 25, an elevated pressure is generated in the pipe 18 by the pump 11, this pressure reaching 10 bars according to the illustrative embodiment. At this pressure, the manometer 22 switches the valve 38 which sits in the by-pass between the pressure pipe 20 and the drain pipe 26. As soon as 10 bars have been reached, the difference signal of the drilling density, obtained simultaneously at the density sensors 32, 33 (high-pressure side, 100bars) and the density sensors 30, 31 (low-pressure side), is fed to the computer 27. At the same time, the valve 38 opens, and the elevated pressure which applies and, accordingly, the manometer fall. Hence, the measuring path is ready for a new control signal as soon as 10 bars are reached again.

The relief valve 40 responds if a pressure which is higher than that set at 38, arises.

The input of the pressures measured under the pressure in the pipe 6 and under the elevated pressure in the pipe 20 results in a factor which exactly reproduces the gas content of the drilling fluid.

Figure 2:
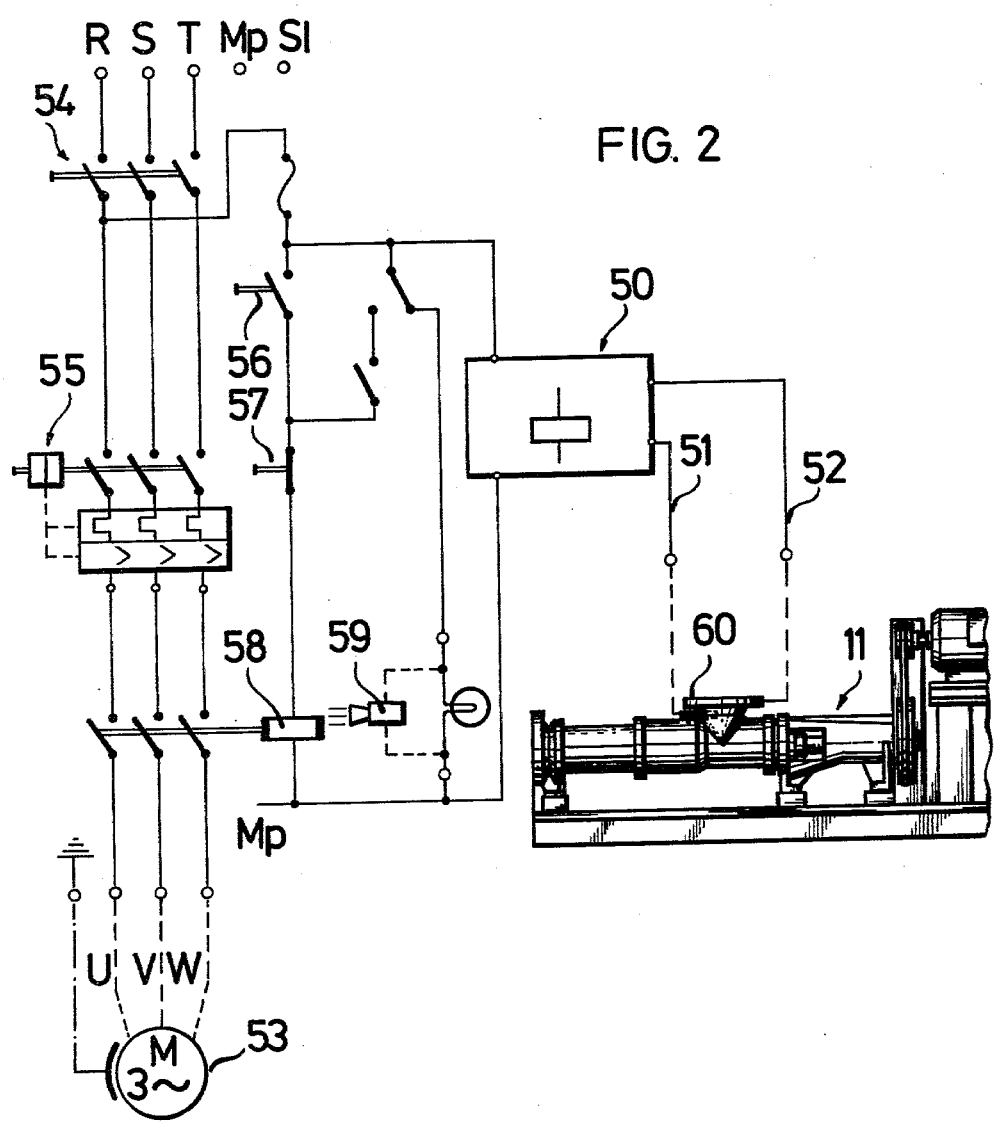
FIG. 2 shows a device which can be used in the equipment according to FIG. 1.

The circuit reproduced in FIG. 2 shows a control instrument 50 having lines 51 and 52 leading to the pump 11. The motor of the pump is shown at 53 and can be switched on by means of the main switch indicated at 54. A motor-protection circuit breaker 55 is provided. A pushbutton switch 56 serves for switching on, while a further pushbutton switch 57 is actuated for switching the pump off. The device has the purpose of preventing the pump from running dry. In effect, when the electrode shown at 60 becomes dry, the drilling fluid present is no longer sufficient for the pump 11. The control instrument then triggers the contactor 58 and gives an acoustic alarm at 59.

Figure 3:
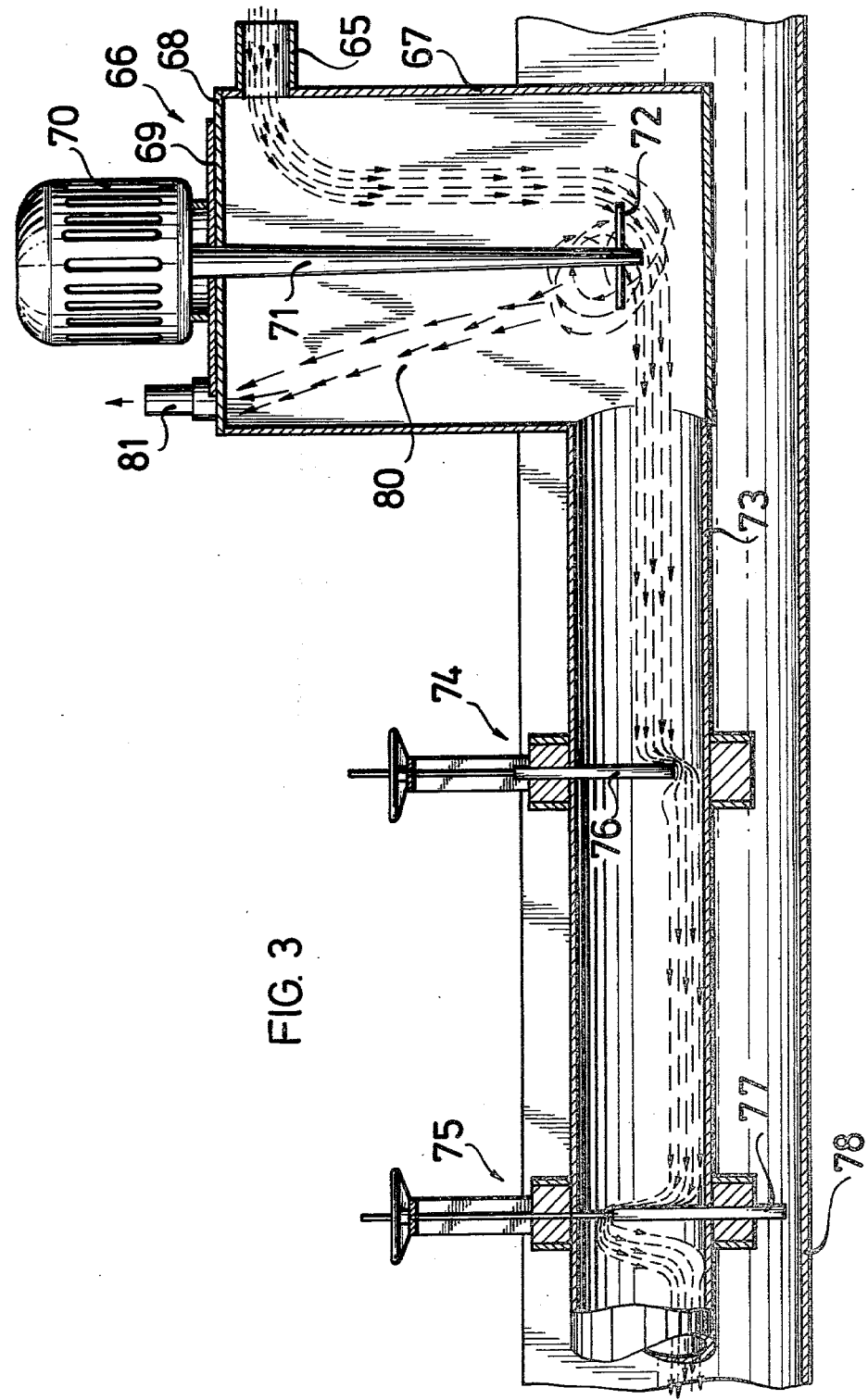
FIG. 3 shows a gas-sampling device for the qualitative gas analysis.

An inlet pipe 65, only a part of which can be seen in FIG. 3, is connected to the flange 43. The drilling fluid, the gas content of which has been quantitatively determined by means of the measuring arrangement described, is passed through this pipe into a device which is generally designated as 66 and which serves to provide the prerequisites for qualitative gas analysis.

The device 66 has a drilling fluid box 67, the pipe 65 ending in the top thereof. A degassing motor 70 the shaft 71 of which forms an agitator, the blade of which is shown at 72, is fixed to the cover 68 with the aid of a plate 69. The box 67 has a drain pipe 73 in which two slide valves 74 and 75 are inserted in series. The slide valves form weirs 76 and 77 which constrict the cross-section of the drain pipe 73 from above and from below. According to the illustrative embodiment shown, the cross-section is first restricted from above by the first slide valve 74 with the weir 76 and it is restricted from below by the second slide valve 75 with the aid of the weir 77. Moreover, the drain pipe 73 ends in the drilling fluid channel 78 which also receives the part of the drilling fluid, which runs out of the standpipe.

A liquid-tight closure of the drainpipe 73 in the box 67 is possible by means of the slide valves 74 and 75 so that gas which is evolved at 80 can be extracted from the drilling fluid box 67 via a nipple 81. The downstream gas-measuring instruments are not shown, but they make qualitative sampling of the gases possible.

Figure 4:
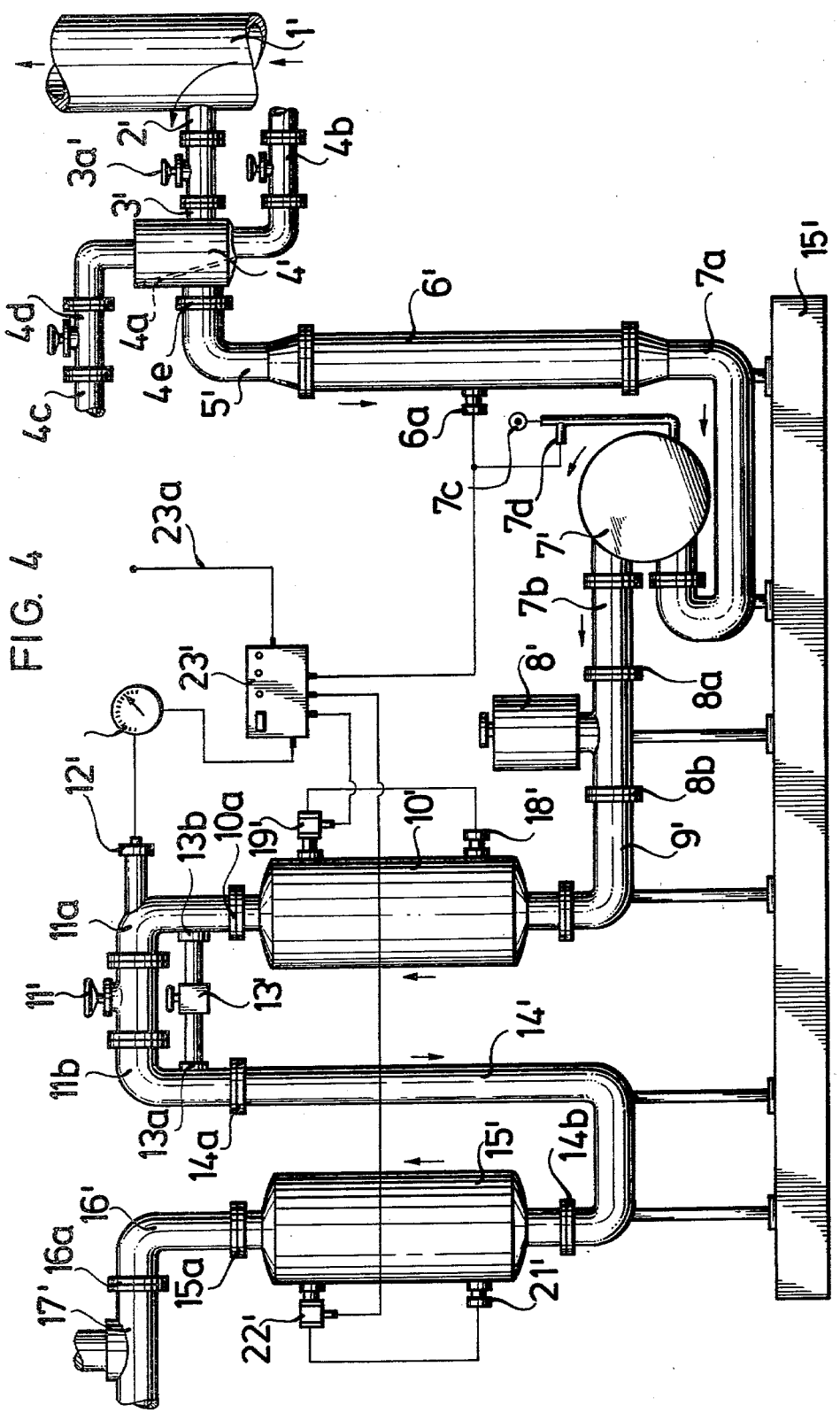
FIG. 4 shows a modified embodiment, in a representation corresponding to that of FIG. 1.

In the embodiment according to FIG. 4, the drilling fluid coming up from a deep well to the surface also is present in a standpipe 1, as in the embodiment according to FIG. 1. Above a blow-out preventer which is not shown and below the drilling fluid outlet, the branch 2', which has a filter strainer screwed in, branches off.

Under a pressure which is given by the well outlet, that is to say the known atmospheric and relatively low pressure, the drilling fluid enters through the connecting pipe 3' having an isolation valve 3a' into the cuttings separator 4' and into the actual measuring equipment.

The screen 4a is installed in the cuttings separator 4' so that the fluid is again separated from coarse drillings and can run out via the outlet branch 4b with an isolation valve, or when the latter is opened, the coarse drilling fluid can by-pass the measuring equipment.

Furthermore, the cuttings separator is fitted with a water feed branch 4c with an isolation valve 4d in order to make it possible occasionally to clean it and to flush away the coarse drillings via the outlet/by-pass branch 4b. Via the measuring feed branch 4e, the drilling fluid runs through the pipe connection 5' into the upright measuring pipe 6'.

The branch 6a for the temperature sensor is fitted to the measuring pipe 6'. The measuring pipe 6' is connected via a pipe system to the suction nozzle 7a of an extraction pump 7' which is driven by compressed air and which presses the drilling fluid from the suction via the delivery nozzles 7b and 8a into the pressure equalisation vessel 8'.

The pressure pump 7' is supplied with compressed air for operation via the connection 7c and it is switched via the explosion-proofed solenoid valve 7d. The operating control of the valve for the compressed air for operation is effected by the temperature sensor 6a via the electronic computer 23'.

From the outlet branch 8b of the pressure equalisation vessel, the drilling fluid is pressed under pressure via the flanged-on pipe length 9' into the upright measuring pipe 10'. Differential density meters 18' and 19' for measuring the weight of the drilling fluid under the action of the pump pressure which applies (true-mud-weight) are fitted at the lower and upper ends of the measuring tube 10' at a distance of exactly 700 mm. An electrical connection leads from the sensor unit 18' and 19' to the computer 23'. The measured signal is transmitted from there (23a).

The outlet nozzle 10a is fitted to the top of the measuring pipe 10', and the pressure control valve 11' which is adjustable from 0-10 bars and which has the pipe connections 11a and 11b is flanged in the form of a U to the outlet nozzle 10a. Furthermore, a remote-sensing manometer for monitoring the pressure set on the pressure reducer 11' is fitted to the delivery nozzle 11a, together with a long-distance line to the computer 23'. Moreover, the U-shaped flanges 11a and 11b are directly joined to the connecting branch 13a, 13b via an interposed by-pass relief valve 13'. The connecting branch 11b is flanged via 14a to the fall pipe 14' and leads via the connecting branch 14b into the final upright measuring pipe 15' (low pressure).

Exactly as in the measuring pipe 10', the differential density meters 21' and 22' for measuring the drilling fluid weight without pressure (apparent-mud-weight) are fitted to the lower and upper ends of the measuring pipe 15'. An electrical connection leads from the sensor unit 21' and 22' to the computer 23'. The measured signal is transmitted from there.

At the top of the measuring pipe 15', via the nozzle 15a, the outlet low-pressure pipes 16' are flanged via the connecting nozzle 16a to the degassing system 17' for sampling the gases for the purpose of qualitative gas analysis.

The entire unit is mounted on a light-weight base frame.

The equipment described operates as follows:

In the measuring pipe 6', the drilling fluid is under a low initial pressure which results from the level difference of the nozzle 2'. Through the cuttings separator 4', the drilling fluid passes, without the so-called cuttings, into the measuring pipe 6' and hence to the sensor 6a for measuring the temperature.

The pump 7' extracts the solids fraction and the screened drilling fluid via the connecting pipes 7a. Under a pressure set by the valve 11 (range 0–10 bars), the fluid is pressed into the upright measuring pipe 10'. The drilling fluid is thus compressed up to, for example, 10 bars with the aid of the pump 7'. Under this pressure, the density of the drilling fluid is measured by the sensors 18' and 19'. These values are fed on to the computer 23'. The set pressure is monitored by a special remote-sensing manometer 12'.

Due to the valve settings 11' and 13', the relief valve 13' opening at an elevated pressure of 10 bars, an elevated pressure is generated in the measuring pipe 10' by the pump 7'. When a pressure higher than 10 bars is reached, the relief valve 13' which is fitted in the by-pass between the connecting nozzles 13a and 13b, is actuated.

Downstream of the valve 11', the drilling fluid enters under a low pressure via the line system 14' into the second measuring pipe 15'. The density of the drilling fluid is measured again on the measuring sensors 21' and 22'. These values are fed to the computer 23'.

A factor which accurately reproduces the gas content of the drilling fluid is obtained from the input of the pressures measured under the elevated pressure in the measuring pipe 10' and under the low pressure in the measuring pipe 15'.

Figure 5:
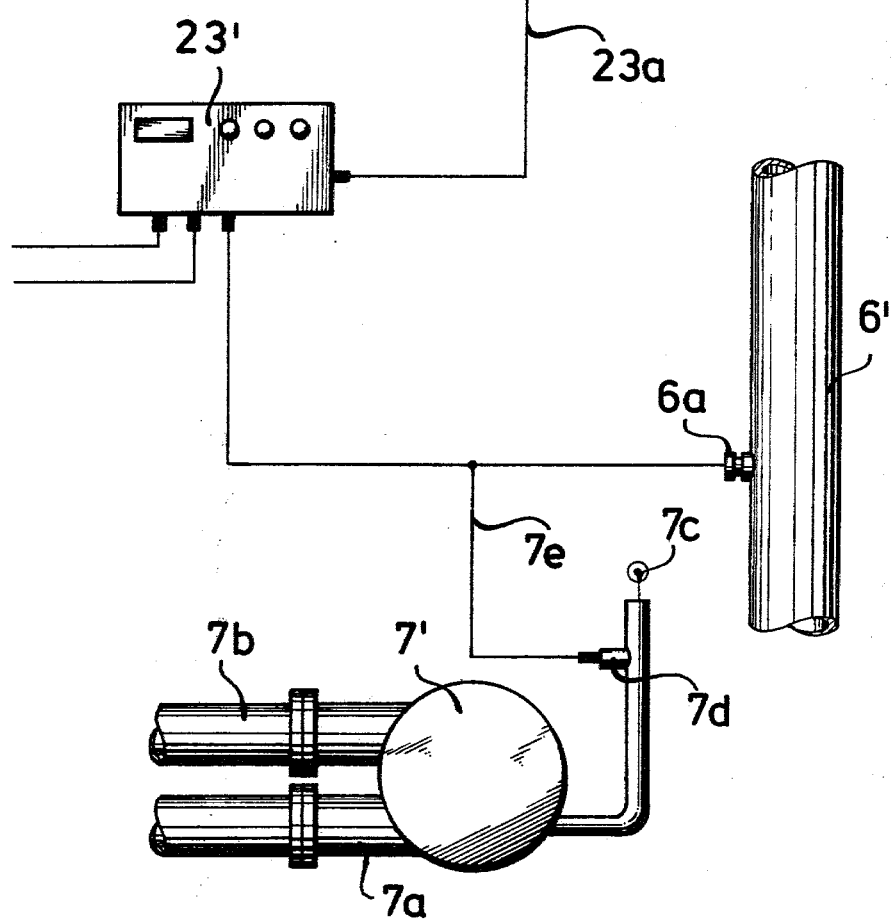
FIG. 5 shows equipment, corresponding to FIG. 2.

The circuit reproduced in FIG. 5 shows the control system which is operated by the computer 23' and which comprises the input lines 7e to the explosion-proofed solenoid valve 7d, and the compressed-air connection 7c to the pump 7' which is driven by compressed air. The compressed-air pump is shown as 7' and it can be switched on by the temperature sensor 6a as a result of the computer 23' of the solenoid valve 7d making an electric contact.

The device has the purpose of preventing the pump from running dry. In fact, if the temperature set in the computer 23' is not scanned by 6a, no drilling fluid flows through the measuring pipe 6' and the unit remains out of operation.

Details about the construction of the degasser 17, used in the device according to FIG. 4 for the qualitative gas analysis, can be seen from FIG. 3. The degasser 17' is joined to the outlet of the measuring pipe 15a by the flange 16a via the connector 16'.

The drilling fluid, the gas content of which has been quantitatively determined by means of the measuring arrangement described, is passed through this pipe into the device which is drawn in FIG. 3 and which serves to provide the prerequisites for qualitative gas analysis.

We claim:

1. A process for measuring the gas content of a loaded, well drilling fluid comprising the steps of:
   obtaining a sample of the fluid from the well;
   supplying the fluid sample to a first chamber having a first pressure condition therein;
   ascertaining the density of the drilling fluid under the first pressure condition;
   removing the fluid sample from said first chamber and supplying same to a second chamber having a second pressure condition therein different from the first pressure condition;
   ascertaining the density of the drilling fluid under the second pressure condition; and
   determining, by means of the densities ascertained under the first and second pressure conditions, the gas content of the drilling fluid.

2. The process according to claim 1 further defined as establishing the pressure of said second pressure condition in the second chamber higher than the pressure of the first pressure condition in the first chamber.

3. The process according to claim 2 further defined as establishing the first pressure condition as that under which the fluid emerges from the well.

4. The process according to claim 1 further defined as establishing the pressure of said second pressure condition in the second chamber lower than pressure of the first pressure condition in the first chamber.

5. The process according to claim 4 further defined as pressurizing the fluid to the first pressure condition as it emerges from the well and thereafter relieving the pressure on said fluid to the second pressure condition.

6. The process according to claim 1 wherein the ascertaining steps are further defined as measuring the differential hydrostatic pressure in a column of fluid of predetermined height.

7. The process according to claim 6 wherein the ascertaining steps are further defined as carried out in columns of similar height commencing at similar reference datum.

8. The process according to claim 1 including the step of removing at least a portion of the gas content of the drilling fluid and quantitatively analyzing same.

9. Apparatus for determining the gas content of a loaded, well drilling fluid comprising:
a first, generally vertical column for receiving the drilling fluid as it emerges from the well, said column having means for ascertaining the density of drilling fluid contained therein;
a second, generally vertical column for receiving the drilling fluid from the first column, said column having means for ascertaining the density of drilling fluid contained therein;
means coupled to said one of first and second columns for providing a different pressure condition in one of said columns than in the other; and
means coupled and responsive to said density ascertaining means for indicating the gas content of the drilling fluid.

10. The apparatus according to claim 9 wherein said means for providing a different pressure condition in one of said columns comprises pressurizing means.

11. The apparatus according to claim 10 wherein said pressurizing means is coupled to said first column.

12. The apparatus according to claim 10 wherein said pressurizing means is coupled to said second column.

13. The apparatus according to claim 10 wherein said pressurizing means comprises a pump.

14. The apparatus according to claim 13 including means for preventing said pump from running dry.

15. The apparatus according to claim 9 including pressure relief means coupled to the column of higher pressure.

16. The apparatus according to claim 15 further including over-pressure protection means coupled to the column of higher pressure.

17. The apparatus according to claim 9 including means for removing and quantitatively analyzing at least a portion of the gas content of the drilling fluid.

18. The apparatus according to claim 9 including an inlet screen coupled to one of said columns for screening said fluid.

* * * * *